US012110529B2

(12) United States Patent
Terrill (10) Patent No.: US 12,110,529 B2
(45) Date of Patent: Oct. 8, 2024

(54) METHODS AND SYSTEMS USING IONOPHORES TO CONTROL CONTAMINATION IN FERMENTATION OF GASEOUS SUBSTRATES

(71) Applicant: Synata Bio, Inc., Warrenville, IL (US)

(72) Inventor: Jennine B. Terrill, Chicago, IL (US)

(73) Assignee: Synata Bio, Inc., Warrenville, IL (US)

( * ) Notice: Subject to any disclaimer, the term of this patent is extended or adjusted under 35 U.S.C. 154(b) by 1104 days.

(21) Appl. No.: 16/471,453

(22) PCT Filed: Dec. 14, 2017

(86) PCT No.: PCT/US2017/066450
§ 371 (c)(1),
(2) Date: Jun. 19, 2019

(87) PCT Pub. No.: WO2018/118650
PCT Pub. Date: Jun. 28, 2018

(65) Prior Publication Data
US 2021/0130851 A1 May 6, 2021

Related U.S. Application Data

(60) Provisional application No. 62/438,211, filed on Dec. 22, 2016.

(51) Int. Cl.
*C12P 7/06* (2006.01)
*C12M 1/00* (2006.01)
*C12P 7/40* (2006.01)

(52) U.S. Cl.
CPC ............. *C12P 7/065* (2013.01); *C12M 21/12* (2013.01); *C12M 43/02* (2013.01)

(58) Field of Classification Search
CPC ... C12N 15/10; C12N 1/20; C12P 7/14; C12P 7/16; C12P 7/54; C12P 7/6409; C12Y 302/01023
USPC ...................... 435/201, 266, 252.3, 488, 166
See application file for complete search history.

(56) References Cited

U.S. PATENT DOCUMENTS

| 5,173,429 | A | 12/1992 | Gaddy et al. |
| 5,888,788 | A | 3/1999 | De Miniac |
| 2003/0211585 | A1 | 11/2003 | Gaddy et al. |
| 2013/0071896 | A1 | 3/2013 | Reeves et al. |

FOREIGN PATENT DOCUMENTS

| CN | 1090707 | A | 8/1994 |
| CN | 107043792 | A | 8/2017 |
| EP | 0079707 | A1 | 5/1983 |
| JP | H10-229889 | A | 9/1998 |
| JP | 2015-527056 | A | 9/2015 |
| RU | 2104301 | C1 | 2/1998 |
| RU | 2522523 | C1 | 7/2014 |
| WO | WO 1994/008738 | A1 | 4/1994 |
| WO | 02/08438 | A2 | 1/2002 |
| WO | WO 2013/188858 | A2 | 12/2013 |

OTHER PUBLICATIONS

Daniel et al., Characterization of the H2-and CO-Dependent Chemolithotrophic Potentials of the Acetogens *Clostridium thermoaceticum* and *Acetogenium kivui*. *Journal of Bacteriology*, 172:8 4464-4471 (Aug. 1990).
Liew et al., "Gas Fermentation—A Flexible Platform for Commercial Scale Production of Low-Carbon-Fuels and Chemicals from Waste and Renewable Feedstocks," *Frontiers in Microbiology*, 7: 1-28 (May 2016).
Leclerc et al., H2/C02 Metabolism in Acetogenic Bacteria Isolated From the Human Colon, *Anaerobe*, 3:5, 307-315 (Jan. 1997).
European Patent Office, International Search Report and the Written Opinion in International Application No. PCT/US2017/066450 (Jun. 15, 2018).
Federal Service for Intellectual Property Federal Institute of Industrial Property, Search Report in Russian Application No. 2019122805 (Apr. 14, 2021).
China National Intellectual Property Administration, Office Action in Chinese Patent Application No. 201780084255.2 (Oct. 10, 2022).
Abrini et al., "*Clostridium autoethanogenum*, sp. nov., an anaerobic bacterium that produces ethanol from carbon monoxide," *Arch. Microbiol.*, 161: 345-351 (1994).
Guo, "Screening of a Microbial Strain Capable of Producing Ethanol from Syngas Fermentation," *Guangxi Sciences*, 21(2): 124-128 (2014).
China National Intellectual Property Administration, Office Action in Chinese Patent Application No. 201780084255.2 (Nov. 17, 2023).
Heise et al., "Sodium Dependence of Acetate Formation by the Acetogenic Bacterium *Acetobacterium woodii,*" *Journal of Bacteriology*, 171(10): 5473-5478 (1989).

(Continued)

*Primary Examiner* — Tekchand Saidha
*Assistant Examiner* — Mohammad Y Meah
(74) *Attorney, Agent, or Firm* — Leydig, Voit & Mayer, Ltd.

(57) ABSTRACT

Provided is a method of anaerobically fermenting a gaseous substrate to form a liquid product, the method comprising: (a) introducing the gaseous substrate into a bio-reactor, the gaseous substrate comprising at least one of the following constituents: carbon monoxide, carbon dioxide, and hydrogen, (b) the bio-reactor comprising a fermentation broth therein, the fermentation broth containing at least two types of microorganisms, one type comprising at least one fermenting species, and the other type comprising at least one competing species; (c) introducing at least one type of ionophore into the reactor, the ionophore having selectivity for preferentially inhibiting the at least one competing species from growing and/or producing an undesired product; and (d) allowing the gaseous substrate to ferment by exposure to the at least one fermenting species, to produce the liquid product and a system for doing the same.

19 Claims, 1 Drawing Sheet

(56) References Cited

OTHER PUBLICATIONS

Japanese Patent Office, Decision of Refusal in Japanese Patent Application No. 2019-534883 (Apr. 5, 2022).
Rezayi et al., "Immobilization of Ionophore and Surface Characterization Studies of the Titanium(III) Ion in a PVC-Membrane Sensor," *Sensors*, 12(7): 8806-8814 (2012).
Canadian Patent Office, Office Action in Canadian Patent Application No. 3,047,764 (Dec. 1, 2023).

METHODS AND SYSTEMS USING IONOPHORES TO CONTROL CONTAMINATION IN FERMENTATION OF GASEOUS SUBSTRATES

CROSS-REFERENCE TO RELATED APPLICATIONS

This patent application is the U.S. national phase of International Application No. PCT/US2017/066450, filed Dec. 14, 2017, which, claims the benefit of priority to U.S. Provisional Patent Application No. 62/438,211, filed Dec. 22, 2016, and entitled, "Methods And Systems Using Ionophores To Control Contamination In Fermentation Of Gaseous Substrates," which are incorporated by reference in their entireties herein.

BACKGROUND OF THE INVENTION

Ethanol is the primary source of biofuel worldwide and thus, new methods of bioethanol production are highly sought after. Conventionally, biofuels, and more specifically bioethanol, are produced from fermentation of sugars derived from, for example, corn, wheat, and sugar cane. This process is highly desirable because the use or conversion of biomass is a renewable and potentially sustainable source of energy production. However, readily fermentable carbohydrates are limited because of competition with food production, available land and water usage, and other factors.

A highly efficient alternative to production of ethanol by fermentation of carbohydrates, such as glucose and sucrose, is synthesis gas (syngas) fermentation. Syngas fermentation is a microbial process, wherein the primary carbon and energy sources are provided from syngas. Commonly referred to as acetogens, these microorganisms utilize small chemical building blocks, present in syngas, in the reductive Acetyl-CoA pathway (Wood-Ljungdahl pathway), to produce ethanol and/or acetic acid.

Syngas is typically derived from the gasification of carbonaceous materials, reforming of natural gas and/or biogas from anaerobic fermentors, or from various industrial methods. The gas substrate generally comprises carbon monoxide, hydrogen, and carbon dioxide and usually contains other components such as water vapor, nitrogen, methane, ammonia, and hydrogen sulfide. Fermentation of syngas predominantly results in the formation of ethanol and acetic acid. This process requires significant amounts of hydrogen and carbon monoxide. The balanced chemical equations for the overall conversion of carbon monoxide, carbon dioxide, and hydrogen to ethanol and acetic acid are as follows:

Ethanol Production $$6CO + 3H_2O \rightarrow C_2H_5OH + 4CO_2$$

$$6H_2 + 2CO_2 \rightarrow C_2H_5OH + 3H_2O$$

Acetic Acid Production $$4CO + 2H_2O \rightarrow CH_3COOH + 2CO_2$$

$$4H_2 + 2CO_2 \rightarrow CH_3COOH + 2H_2O$$

As demonstrated by the balanced chemical equations, both carbon monoxide and carbon dioxide can be used as the primary source of carbon, facilitated by the electrons produced by carbon monoxide and hydrogen.

One of the common problems faced by a continuous, commercial facility for the bioconversion of syngas to ethanol and/or acetic acid is contamination of the fermentation broth with an undesirable population of microorganisms. These contaminating microorganisms convert components of syngas, or products and/or byproducts of the acetogenic bioconversion, to undesired oxygenated organic compounds. The contaminating organisms can also potentially utilize the nutritional components of the growth medium, competing with the desired organism. Reduction or removal of contaminating microorganisms from commercial scale bio-reactors can be challenging and costly. Preventative measures, such as steam cleaning, are often unsuccessful due to incomplete cleaning. In addition, contamination can occur from materials introduced into the bio-reactor during the bioconversion process. Moreover, if a commercial-scale bio-reactor becomes contaminated, the bio-reactor must be taken off-line, its contents discharged with appropriate waste treatment, and the bio-reactor recharged. This process is costly and inefficient.

Methods to reduce or remove competing microorganisms, such as methanogens or butyrogens, which are immune to or thrive on conditions necessary for syngas fermentation, are highly desirable. The present invention is directed to the development of a new technique to mitigate the influence of competing microorganisms.

BRIEF SUMMARY OF THE INVENTION

In one aspect, the invention provides a method of fermenting a gaseous substrate to form a liquid product, the method comprising: (a) introducing the gaseous substrate into a bio-reactor, the bio-reactor comprising a fermentation broth therein, the fermentation broth comprising a fermenting species; (b) introducing at least one type of ionophore into the bio-reactor, the ionophore having selectivity for minimally inhibiting the fermenting species from growing and/or producing the liquid product; and (c) allowing the substrate to ferment to produce the liquid product, wherein the gaseous substrate is the primary carbon source for the fermentation product. It will be understood that the method steps can be in any sequential order, or occur concurrently.

In another aspect, the invention provides a method of fermenting a gaseous substrate to form a liquid product, the method comprising: (a) introducing the gaseous substrate into a bio-reactor, the gaseous substrate comprising at least one of the following constituents: carbon monoxide, carbon dioxide, and hydrogen, the bio-reactor comprising a fermentation broth comprising a fermenting species; (b) introducing at least one type of ionophore into the bio-reactor, the ionophore having selectivity for minimally inhibiting the fermenting species from growing and/or producing the liquid product; and (c) allowing the gaseous substrate to ferment to produce the liquid product, wherein the gaseous substrate is the primary carbon source for the fermentation product. It will be understood that the method steps can be in any sequential order, or occur concurrently.

In another aspect, the invention provides a method of anaerobically fermenting a gaseous substrate to form a liquid product, the method comprising: (a) introducing the gaseous substrate into a bio-reactor, the bio-reactor comprising a fermentation broth therein, the fermentation broth containing at least two types of microorganisms, one type comprising at least one fermenting species, and the other type comprising at least one competing species; (b) introducing at least one type of ionophore into the bio-reactor, the ionophore having selectivity for preferentially inhibiting the at least one competing species from growing and/or producing an undesired product; and (c) allowing the substrate to ferment by exposure to the at least one fermenting species, to produce the liquid product, wherein the gaseous substrate is the primary carbon source for the fermentation product. It will be understood that the method steps can be in any sequential order, or occur concurrently.

In another aspect, the invention provides a method of anaerobically fermenting a gaseous substrate to form a liquid product, the method comprising: (a) introducing the gaseous substrate into a bio-reactor, the gaseous substrate comprising at least one of the following constituents: carbon monoxide, carbon dioxide, and hydrogen, the bio-reactor comprising a fermentation broth therein, the fermentation broth containing at least two types of microorganisms, one type comprising at least one fermenting species, and the other type comprising at least one competing species; (b) introducing at least one type of ionophore into the reactor, the ionophore having selectivity for preferentially inhibiting the at least one competing species from growing and/or producing an undesired product; and (c) allowing the gaseous substrate to ferment by exposure to the at least one fermenting species, to produce the liquid product. It will be understood that the method steps can be in any sequential order, or occur concurrently.

In another aspect, the invention provides a fermentation system for fermenting a gaseous substrate to form a liquid product, the system comprising: (a) a fermentation vessel; (b) a gaseous substrate supply conduit for introducing the gaseous substrate into the fermentation vessel; (c) an aqueous fermentation broth disposed in the fermentation vessel, the fermentation broth comprising a fermenting species; (d) an ionophore supply conduit in communication with the fermentation vessel for introducing at least one type of ionophore into the vessel, the ionophore selected to minimally inhibit the fermenting species from growing and/or producing the liquid product; and (e) a liquid recovery conduit for collecting the liquid product after the gaseous substrate is allowed to ferment. It will be understood that the system components can be supplied and/or assembled in any sequential order or concurrently.

In another aspect, the invention provides a fermentation system for fermenting a gaseous substrate to form a liquid product, the system comprising: (a) a fermentation vessel; (b) a gas supply conduit for introducing the gaseous substrate into the fermentation vessel, the gaseous substrate comprising at least one of the following constituents: carbon monoxide, carbon dioxide, and hydrogen; (c) an aqueous fermentation broth disposed in the fermentation vessel, the fermentation broth comprising a fermenting species; (d) an ionophore supply conduit in communication with the fermentation vessel for introducing at least one type of ionophore into the vessel, the ionophore selected to minimally inhibit the fermenting species from growing and/or producing the liquid product; and (e) a liquid recovery conduit for collecting the liquid product after the gaseous substrate is allowed to ferment. It will be understood that the system components can be supplied and/or assembled in any sequential order or concurrently.

In another aspect, the invention provides a fermentation system for anaerobically fermenting a gaseous substrate to form a liquid product, the system comprising: (a) a fermentation vessel; (b) a gaseous substrate supply conduit for introducing the gaseous substrate into the fermentation vessel; (c) an aqueous fermentation broth disposed in the fermentation vessel, the fermentation broth containing at least two types of microorganisms, one type comprising at least one fermenting species, and the other type comprising at least one competing species; (d) an ionophore supply conduit in communication with the fermentation vessel for introducing at least one type of ionophore into the vessel, the ionophore having selectivity for preferentially inhibiting the at least one competing species from growing and/or producing an undesired product; and (e) a liquid recovery conduit for collecting the liquid product after the gaseous substrate is allowed to ferment by exposure to the at least one fermenting species. It will be understood that the system components can be supplied and/or assembled in any sequential order or concurrently.

In another aspect, the invention provides a fermentation system for anaerobically fermenting a gaseous substrate to form a liquid product, the system comprising: (a) a fermentation vessel; (b) a gas supply conduit for introducing the gaseous substrate into the fermentation vessel, the gaseous substrate comprising at least one of the following constituents: carbon monoxide, carbon dioxide, and hydrogen; (c) an aqueous fermentation broth disposed in the fermentation vessel, the fermentation broth containing at least two types of microorganisms, one type comprising at least one fermenting species, and the other type comprising at least one competing species; (d) an ionophore supply conduit in communication with the fermentation vessel for introducing at least one type of ionophore into the vessel, the ionophore having selectivity for preferentially inhibiting the at least one competing species from growing and/or producing an undesired product; and (e) a liquid recovery conduit for collecting the liquid product after the gaseous substrate is allowed to ferment by exposure to the at least one fermenting species. It will be understood that the system components can be supplied and/or assembled in any sequential order or concurrently.

DETAILED DESCRIPTION OF THE INVENTION

Embodiments of the disclosure provide a method of fermenting a gaseous substrate to provide a liquid product, and a system for doing the same. In some embodiments, the method comprises using a fermenting species for the fermentation of the gaseous substrate, e.g., syngas, to produce a liquid product, such as an alcohol or acid. The fermentation process is often contaminated with one or more competing species, which can be detrimental to liquid production, e.g., the process of ethanol and/or acetic acid production. The present invention uses a surprising and unexpected approach to specifically target the competing species using an ionophore to selectively disrupt ion gradients utilized by the competing species.

It has been found that the intracellular mechanism for adenosine triphosphate ("ATP") production, utilized by the competing species, is slightly different than the mechanisms used by the fermenting species. For example, but without wishing to be bound by any theory, the fermenting species utilizes proton gradients for the production of ATP, whereas the competing species utilizes other ion gradients, such as sodium or potassium gradients. The ionophore is selected to selectively disrupt ion gradients utilized by the competing species.

In an embodiment, the invention provides a method of fermenting a gaseous substrate to form a liquid product, the method comprising: (a) introducing the gaseous substrate into a bio-reactor, the bio-reactor comprising a fermentation broth therein, the fermentation broth comprising a fermenting species; (b) introducing at least one type of ionophore into the bio-reactor, the ionophore having selectivity for minimally inhibiting the fermenting species from growing and/or producing the liquid product; and (c) allowing the substrate to ferment to produce the liquid product, wherein the gaseous substrate is the primary carbon source for the fermentation product.

In some embodiments, the method of anaerobically fermenting a gaseous substrate is a continuous method. As used herein, "continuous method" refers to a fermentation method which includes continuous nutrient feed, substrate feed, cell production in the bio-reactor, cell removal from the bio-reactor, and product removal. In certain embodiments, the continuous feeds, removals or cell production may occur in the same or in different streams. In certain embodiments, the continuous process results in the achievement of a steady state within the bio-reactor. As used herein, "steady state" refers to all process variables (i.e., feed rates and substrate concentrations maintained in the bio-reactor, cell concentration in the bio-reactor and cell removal from the bio-reactor, product removal from the bio-reactor, as well as conditional variables such as temperatures and pressures) being constant over time. At steady-state conditions, the velocity of the dispersion stream leaving the injector is frequently in the range of 0.5 to 5 meters per second and the ratio of gas to motive liquid is in the range of about 1:1 to 3:1 actual cubic meters per cubic meter of motive liquid.

In certain embodiments, the method of anaerobically fermenting a gaseous substrate comprises introducing the gaseous substrate into a bio-reactor. The bio-reactor can be any suitable bio-reactor of any suitable size. In some instances, the bio-reactor comprises a fermentation broth. The fermentation broth can be any suitable fermentation broth and can be added to the bio-reactor in any suitable amount.

In certain embodiments, the fermentation broth will comprise an aqueous suspension of microorganisms and various media supplements. Suitable microorganisms generally live and grow under anaerobic conditions, meaning that dissolved oxygen is essentially absent from the aqueous fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

In various embodiments, the media optionally further comprises one or more constituents selected from the group consisting of vitamins, minerals, metals, and combinations thereof.

In preferred embodiments, the fermentation broth is maintained under anaerobic fermentation conditions including a suitable temperature, say, between 25° C. and 60° C., frequently in the range of about 30° to 40° C. The conditions of fermentation, including the density of microorganisms and aqueous fermentation broth composition are preferably sufficient to achieve the sought conversion efficiency of hydrogen and carbon monoxide.

The fermentation broth can have any suitable pH. For example, the fermentation broth can have a pH of about 1 or more, e.g., about 1.5 or more, about 2 or more, about 2.5 or more, about 3 or more, about 3.5 or more, about 4 or more, about 4.5 or more, about 5 or more, about 5.5 or more, or about 6 or more. Alternatively, or in addition, the fermentation brother can have a pH of about 9 or less, e.g., about 8.5 or less, about 8 or less, about 7.5 or less, about 7 or less, or about 6.5 or less. Thus, the fermentation broth can have a pH bounded by any two of the above endpoints recited for the fermentation broth. For example the fermentation broth can have a pH of about 1 to about 9, e.g., about 1.5 to about 9, about 2 to about 9, about 2.5 to about 9, about 3 to about 9, about 3.5 to about 9, about 4 to about 9, about 4.5 to about 9, about 5 to about 9, about 5.5 to about 9, about 6 to about 9, about 6 to about 8.5, about 6 to about 8, about 6 to about 7.5, about 6 to about 7, about 4 to about 7, about 7 to about 9, about 2 to about 7, about 2.5 to about 7, about 3.5 to about 7, about 4 to about 7, about 4.5 to about 7, about 5 to about 7, about 5.5 to about 7, about 6 to about 7, about 6.5 to about 7, about 2 to about 6, about 2.5 to about 6, about 3 to about 6, about 3.5 to about 6, about 4 to about 6, about 4.5 to about 6, about 5.5 to about 6.

In some embodiments, the rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important. Preferably the feed gas is introduced into the bioreactor in the form of microbubbles. Often the microbubbles have diameters in the range of 0.01 to 0.5, preferably 0.02 to 0.3 millimeter.

In certain embodiments, the bioreactor assembly for syngas bioconversion may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors, including membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

Generally, the substrate depleted gas phase egressing from the aqueous fermentation broth will contain a small fraction of the hydrogen and carbon oxides introduced into the bioreactor assembly as the feed gas. Inert gases such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, water vapor, alcohol and the like volatilized from the aqueous fermentation broth.

In some embodiments, the bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

In certain embodiments, the media further comprises one or more vitamins. The vitamin can be any suitable vitamin. In certain embodiments, the vitamin comprises a nutrient that helps the growth of the at least one fermenting species. An exemplary, but non-limiting list of vitamins includes K—Ca-pantothenate, choline chloride, folic acid, inositol, niacinamide, nicotinic acid, pantothenic acid, pyridoxal HCl, pyridoxine HCl, pyridoxamine, riboflavin, thiamine HCl, biotin, vitamin B12, para-aminobenzoic acid, niacin, ascorbic acid, calciferol, menadione, and vitamin A.

Each of the one or more vitamins can be present in the media in any suitable concentration. The media can comprise about 1 µg/kg or more of each of the one or more vitamins, for example, about 10 µg/kg or more, about 50 µg/kg or more, about 100 µg/kg or more, about 250 µg/kg or more, about 500 µg/kg or more, or about 1000 µg/kg or more. Alternatively, or in addition, the media can comprise about 20000 mg/kg or less of the one or more vitamins, for example, about 15000 mg/kg or less, about 12500 mg/kg or less, about 10000 mg/kg or less, about 8000 mg/kg or less, about 6000 mg/kg or less, about 4000 mg/kg or less, about 3000 mg/kg or less, or about 2000 mg/kg or less. Thus, the media can comprise each of the one or more vitamins in an amount bounded by any two of the aforementioned endpoints. For example, the media can comprise about 1 µg/kg to about 2000 mg/kg of each of the one or more vitamins, about 10 µg/kg to about 2000 mg/kg, about 50 µg/kg to about 2000 mg/kg, about 100 µg/kg to about 2000 mg/kg, about 250 µg/kg to about 2000 mg/kg, about 500 µg/kg to about 2000 mg/kg, about 1000 µg/kg to about 2000 mg/kg, about 1000 µg/kg to about 3000 mg/kg, about 1000 mg/kg to about 4000 mg/kg, about 1000 µg/kg to about 6000 mg/kg, about 1000 µg/kg to about 8000 mg/kg, about 1000 µg/kg to about 10000 mg/kg, about 1000 µg/kg to about 12500 mg/kg, about 1000 µg/kg to about 15000 mg/kg, or about 1000 µg/kg to about 20000 mg/kg.

In certain embodiments, the media further comprises one or more minerals. Generally, the mineral is necessary for maintaining metabolic processes of the fermenting species. The mineral can be any suitable mineral. An exemplary, but non-limiting list of minerals includes any form of nitrogen (e.g., ammonium or ammonia), calcium, chloride, iron, iodine, potassium, molybdenum, magnesium, sulfur (e.g., sulfide, sulfate, sulfite, thiosulfate, or bisulfate), phosphorous (e.g., phosphate), and sodium. In some embodiments, the mineral is provided in the form of a compound or a salt.

Each of the one or more minerals can be present in the media in any suitable concentration. The media can comprise about 0.1 mg/kg or more of each of the one or more minerals as a compound/salt, for example, about 1 mg/kg or more, about 5 mg/kg or more, about 10 mg/kg or more, about 15 mg/kg or more, about 20 mg/kg or more, about 25 mg/kg or more, about 50 mg/kg or more, about 100 mg/kg or more, about 250 mg/kg or more, about 500 mg/kg or more, or about 1000 mg/kg or more. Alternatively, or in addition, the media can comprise about 20000 mg/kg or less of the one or more minerals, for example, about 15000 mg/kg or less, about 12500 mg/kg or less, about 10000 mg/kg or less, about 8000 mg/kg or less, about 6000 mg/kg or less, about 4000 mg/kg or less, about 3000 mg/kg or less, or about 2000 mg/kg or less. Thus, the media can comprise each of the one or more minerals in an amount bounded by any two of the aforementioned endpoints. For example, the media can comprise about 0.1 mg/kg to about 2000 mg/kg of each of the one or more minerals, about 1 mg/kg to about 2000 mg/kg, about 5 mg/kg to about 2000 mg/kg, about 10 mg/kg to about 2000 mg/kg, about 15 mg/kg to about 2000 mg/kg, about 20 mg/kg to about 2000 mg/kg, about 25, mg/kg to about 2000 mg/kg, about 50 mg/kg to about 2000 mg/kg, about 100 mg/kg to about 2000 mg/kg, about 250 mg/kg to about 2000 mg/kg, about 500 mg/kg to about 2000 mg/kg, about 1000 mg/kg to about 2000 mg/kg, about 1000 mg/kg to about 3000 mg/kg, about 1000 mg/kg to about 4000 mg/kg, about 1000 mg/kg to about 6000 mg/kg, about 1000 mg/kg to about 8000 mg/kg, about 1000 mg/kg to about 10000 mg/kg, about 1000 mg/kg to about 12500 mg/kg, about 1000 mg/kg to about 15000 mg/kg, or about 1000 mg/kg to about 20000 mg/kg.

In certain embodiments, the media further comprises one or more metals. Generally, the metal is necessary for maintaining metabolic processes of the fermenting species. The metal can be any common metal. Generally, the metal is biologically relevant. An exemplary, but non-limiting list of metals includes lithium, manganese, cobalt, nickel, copper, gallium, arsenic, selenium, aluminum, silicon, phosphorous, molybdenum, zirconium, silver, palladium, zinc, tungsten, and cadmium. In some embodiments, the metal is provided in the form of a compound or a salt.

Each of the one or more metals can be present in the media in any suitable concentration. The media can comprise about 0.1 mg/kg or more of each of the one or more metals as a compound/salt, for example, about 1 mg/kg or more, about 5 mg/kg or more, about 10 mg/kg or more, about 15 mg/kg or more, about 20 mg/kg or more, about 25 mg/kg or more, about 50 mg/kg or more, about 100 mg/kg or more, about 250 mg/kg or more, about 500 mg/kg or more, or about 1000 mg/kg or more. Alternatively, or in addition, the media can comprise about 20000 mg/kg or less of the one or more metals, for example, about 15000 mg/kg or less, about 12500 mg/kg or less, about 10000 mg/kg or less, about 8000 mg/kg or less, about 6000 mg/kg or less, about 4000 mg/kg or less, about 3000 mg/kg or less, or about 2000 mg/kg or less. Thus, the media can comprise each of the one or more metals in an amount bounded by any two of the aforementioned endpoints. For example, the media can comprise about 0.1 mg/kg to about 2000 mg/kg of each of the one or more metals, about 1 mg/kg to about 2000 mg/kg, about 5 mg/kg to about 2000 mg/kg, about 10 mg/kg to about 2000 mg/kg, about 15 mg/kg to about 2000 mg/kg, about 20 mg/kg to about 2000 mg/kg, about 25, mg/kg to about 2000 mg/kg, about 50 mg/kg to about 2000 mg/kg, about 100 mg/kg to about 2000 mg/kg, about 250 mg/kg to about 2000 mg/kg, about 500 mg/kg to about 2000 mg/kg, about 1000 mg/kg to about 2000 mg/kg, about 1000 mg/kg to about 3000 mg/kg, about 1000 mg/kg to about 4000 mg/kg, about 1000 mg/kg to about 6000 mg/kg, about 1000 mg/kg to about 8000 mg/kg, about 1000 mg/kg to about 10000 mg/kg, about 1000 mg/kg to about 12500 mg/kg, about 1000 mg/kg to about 15000 mg/kg, or about 1000 mg/kg to about 20000 mg/kg.

The gaseous substrate can be any suitable gaseous substrate. In some embodiments, the gaseous substrate comprises one or more gases selected from the group consisting of carbon monoxide, carbon dioxide, and hydrogen. In a preferred embodiment, the gaseous substrate is syngas. As used herein, "syngas" refers to a gaseous substrate comprising carbon monoxide, carbon dioxide, and hydrogen. The gaseous substrate may optionally contain water vapor, nitrogen, methane, ammonia, and hydrogen sulfide. In certain embodiments, the gaseous substrate is the primary source of carbon for the one or more alcohols or acids.

The gaseous substrate can be prepared in any suitable manner. In some embodiments, the gaseous substrate is prepared from gasification of a solid substrate. The solid substrate can be any suitable solid substrate capable of being gasified. Typically, the solid substrate is selected from the group consisting of biomass, woodchips, municipal solids, coal, and combinations thereof. In some embodiments, the gaseous substrate is prepared from reforming a gaseous precursor. The gaseous precursor can be any suitable gaseous precursor capable of being reformed. In certain embodiments, steam is used in the reforming of the gaseous substrate. In certain embodiments, the gaseous precursor is methane.

The gaseous substrate can be added during any step of the fermenting process. In certain embodiments, the introduction of the gaseous substrate can be continuous, segmented, semi-continuous, or combinations thereof. As used herein, "continuous" refers to an operation, process, or action that is steady and uninterrupted. As used herein, "segmented" refers to an operation, process, or action that ceases for a time and begins again. As used herein, "semi-continuous" refers to an operation, process, or action, that changes speed for a time and returns to the intended rate. In some instances, the gaseous substrate is scrubbed. As used herein, "scrubbed" refers to the removal of particulates, contaminants, or undesired gases. In some embodiments, the gaseous substrate is partially oxidized.

In some embodiments, the fermentation broth contains one or more microorganisms. The microorganism can be any suitable microorganism. In some instances, the microorganism is one or more fermenting species, competing species, or combinations thereof.

In some instances, the microorganism is at least one fermenting species. The fermenting species can be any suitable fermenting species. In certain embodiments, the fermenting species is a C1 fixing organism. In some embodiments, the fermenting species is an acetogen, homoacetogen, or combinations thereof. Typically, the fermenting species uses hydrogen gradients for adenosine triphosphate ("ATP") production.

Generally, the fermenting species is selected from *Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum, Treponema primitia*, and combinations thereof.

In some instances, the microorganism is at least one competing species. The competing species can be any competing species. Generally, the competing species is considered a contaminant. The competing species can use any suitable ion gradient for the generation of ATP. In certain embodiments, the competing species uses sodium and/or potassium gradients for ATP production.

Generally, the competing species is selected from *Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum, Treponema primitia*, and combinations thereof.

It will be understood that in some embodiments, one or more microorganisms will be targeted as the desired fermenting species, resulting in all other microorganisms becoming the competing species. In another embodiment, a different one or more microorganism will be targeted as the desired fermenting species, resulting in all other microorganisms becoming competing species. It will be understood that in certain environments a certain microorganism is a fermenting species, and in other environments, said microorganism is a competing species.

The bio-reactor further comprises one or more ionophores. The ionophore can be any suitable ionophore. Without wishing to be bound to any theory, the ionophore helps to reduce the competing species by inhibiting the production of ATP. Without wishing to be bound by any theory, the production of ATP is limited by regulation of the ion gradients. The ionophore can regulate any ion gradient. For example, the ionophore can regulate $H^+$ gradients, $Li^+$ gradients, $Na^+$ gradients, $K^+$ gradients, $Mg^{2+}$ gradients, $Ca^{2+}$ gradients, $NH_4^+$ gradients, and combinations thereof. In preferred embodiments, the ionophore selectively targets $Na^+$ gradients, $K^+$ gradients, and combinations thereof.

The ionophore can be any molecule capable of reversibly binding an ion. In some embodiments, the ionophore is a crown ether-based ionophore. In some embodiments, the ionophore is an antibiotic. Typically, the ionophore is selected from the group consisting of 12-crown-4, 15-crown-6, 18-crown-6, dibenzo-18-crown-6, and diaza-18-crown-6, A23187, 4-bromo-A23187, alamethicin, beauvericin, bapta(AM), calcimycin, cezomycin, carbonyl cyanide m-chlorophenyl hydrazone, CA 1001, enniatin, gramicidin A, hellebrin, ionomycin, lasalocid, monesin, nigericin, nonactin, phenamil methanesulfonate, salinomycin, tetonasin, ETH2120, ETH 227, ETH 157, 2,3:11,12-Didecalino-16-crown-5, DD-16-C-5, ETH 4120, Dodecylmethylmalonic acid bis[(12-crown-4)methyl ester], Bis[(12-crown-4)methyl]2,2-didodecylmalonate, 4-tert-Butylcalix[4]arene-tetraacetic acid tetraethyl ester, BME 44, valinomycin and combinations thereof.

The ionophore can be added during any step of the fermenting process. For example, the ionophore can be added prior to the fermentation broth, concurrently with the fermentation broth, or after the fermentation broth. In certain embodiments, the introduction of the ionophore can be continuous, segmented, semi-continuous, or combinations thereof. In some instances, the ionophore is introduced using a liquid feed. In some embodiments, the ionophore is soluble in the liquid feed and/or the fermentation broth. The liquid feed can be added to the bio-reactor in any suitable amount.

The liquid feed can comprise about 100 mM or less of the ionophore, for example, about 90 mM or less, about 80 mM or less, about 70 mM or less, about 60 mM or less, or about 50 mM or less. Alternatively, or in addition to, the liquid feed can comprise about 0.1 µM or more of the ionophore, for example, about 0.25 µM or more, about 0.5 µM or more, about 1 µM or more, about 5 µM or more, about 10 µM or more, or about 20 µM or more. Thus, the liquid feed can comprise an ionophore in a concentration bounded by any two of the aforementioned endpoints. The liquid feed can comprise from about 0.1 µM to about 50 mM ionophore, for example, from about 0.25 µM to about 50 mM, from about 0.5 µM to about 50 mM, from about 1 µM to about 50 mM, from about 5 µM to about 50 mM, from about 10 µM to about 50 mM, from about 20 µM to about 50 mM, from about 20 µM to about 100 mM, from about 20 µM to about 90 mM, from about 20 µM to about 80 mM, from about 20 µM to about 70 mM, from about 20 µM to about 60 mM, or from about 0.1 µM to about 100 mM ionophore.

In some instances, the ionophore is immobilized. The ionophores can be immobilized by any suitable immobilization technique. In some instances, the ionophores are immobilized in a porous particle. In certain embodiments, the immobilization occurs by using the electron force between the ionophore and the porous particle. In certain embodiments, the immobilized ionophore can be removed by centrifugation.

In some instances, the ionophore is not entirely soluble in the liquid feed and/or the fermentation broth. In certain embodiments, the ionophore forms a colloidal suspension in the liquid feed and/or the fermentation broth. In other embodiments, the ionophore is chelated to one or more metal ions. The chelating ionophore can be soluble or insoluble in the liquid feed and/or the fermentation broth. In some embodiments, the chelating ionophore is not entirely soluble in the liquid feed and/or the fermentation broth. In certain embodiments, the not entirely soluble ionophore can be removed by centrifugation.

Each of the one or more ionophores can be present in the fermentation broth in any suitable concentration. The fermentation broth can comprise about 1 µg/kg or more of each of the one or more ionophores, for example, about 10 µg/kg or more, about 50 µg/kg or more, about 100 µg/kg or more, about 250 µg/kg or more, about 500 µg/kg or more, or about 1000 µg/kg or more. Alternatively, or in addition, the fermentation broth can comprise about 20000 mg/kg or less of the one or more ionophores, for example, about 15000 mg/kg or less, about 12500 mg/kg or less, about 10000 mg/kg or less, about 8000 mg/kg or less, about 6000 mg/kg or less, about 4000 mg/kg or less, about 3000 mg/kg or less, or about 2000 mg/kg or less. Thus, the fermentation broth can comprise each of the one or more ionophores in an amount bounded by any two of the aforementioned endpoints. For example, the fermentation broth can comprise about 1 µg/kg to about 2000 mg/kg of each of the one or more ionophores, about 10 µg/kg to about 2000 mg/kg, about 50 µg/kg to about 2000 mg/kg, about 100 µg/kg to about 2000 mg/kg, about 250 µg/kg to about 2000 mg/kg, about 500 µg/kg to about 2000 mg/kg, about 1000 µg/kg to about 2000 mg/kg, about 1000 µg/kg to about 3000 mg/kg, about 1000 µg/kg to about 4000 mg/kg, about 1000 µg/kg to about 6000 mg/kg, about 1000 µg/kg to about 8000 mg/kg, about 1000 µg/kg to about 10000 mg/kg, about 1000 µg/kg to about 12500 mg/kg, about 1000 µg/kg to about 15000 mg/kg, or about 1000 µg/kg to about 20000 mg/kg.

In some embodiments, the ionophore has selectivity for minimally inhibiting the fermenting species from growing and/or producing a liquid product. As used herein, "minimally inhibiting" refers to the fermenting species maintaining at least about 75% of the growth and/or production of a liquid product relative to an equivalent system absent an ionophore. In some embodiments, the fermenting species maintains at least about 85% of the growth and/or production of a liquid product relative to an equivalent system absent an ionophore. In preferred embodiments, the fermenting species maintains at least about 90% of the growth and/or production of a liquid product relative to an equivalent system absent an ionophore. In certain embodiments, the fermenting species maintains 100% of the growth and/or production of a liquid product relative to an equivalent system absent an ionophore (i.e., minimally inhibiting encompasses no inhibition of the fermenting species).

In some embodiments, the ionophore has selectivity for preferentially inhibiting the at least one competing species from growing and/or producing an undesired product. As used herein, "preferentially inhibiting" refers to the ionophore inhibiting the growth and/or production of an undesired product by the competing species in a ratio of at least about 2:1, relative to the growth and production of the fermenting species. For example, the fermenting species maintains at least about 75% of the growth and/or production of the liquid product and the competing species is limited to less than about 50% of the growth and production of the undesired product, relative to an equivalent system absent an ionophore. In some embodiments, the ionophore inhibits the growth and/or production of an undesired product by the competing species in a ratio of at least about 4:1, relative to the growth and production of the fermenting species. In preferred embodiments, the ionophore inhibits the growth and/or production of an undesired product by the competing species in a ratio of at least about 10:1, relative to the growth and production of the fermenting species.

In various embodiments, the ionophore inhibits the level of competing species by preventing the growth of the competing species, killing the competing species, and/or disabling the function of the competing species. In some embodiments, the presence of an ionophore results in a fermentation broth substantially free of a competing species relative to an equivalent fermentation broth absent of an ionophore. As used herein, "substantially free" refers to less than 10% of the competing species relative to a fermentation broth absent of an ionophore. In some embodiments, "substantially free" refers to less than 1% of the competing species relative to an equivalent fermentation broth absent of an ionophore. In preferred embodiments, "substantially free" refers to trace amounts of the competing species relative to an equivalent fermentation broth absent of an ionophore.

In some instances, the bio-reactor further comprises one or more base additions. The base can be any suitable base. Typically, the base is selected from the group consisting of lithium hydroxide, sodium hydroxide, potassium hydroxide, magnesium hydroxide, calcium hydroxide, lithium carbonate, lithium bicarbonate, sodium carbonate, sodium bicarbonate, potassium carbonate, and potassium bicarbonate. In preferred embodiments, the base comprises hydroxide ions.

In some embodiments, the method of fermenting a gaseous substrate forms a liquid product. Generally, the liquid product comprises one or more compounds selected from the group consisting of alcohols, acids, and combinations thereof. In some embodiments, the liquid product is one or more alcohols. The alcohol can be any suitable alcohol. Typically, the alcohol is selected from the group consisting of ethanol, n-propanol, iso-propanol, n-butanol, iso-butanol, n-pentanol, n-hexanol, and combinations thereof. In some embodiments, the liquid product is one or more acids. The acids can be any suitable acids. Typically, the acid is selected from the group consisting of acetic acid, propanoic acid, butanoic acid, pentatonic acid, hexanoic acid, and combinations thereof.

In some instances, the liquid product is produced by a microorganism within the fermentation broth, resulting in a fermentation mixture. In certain embodiments, a portion of the fermentation mixture is withdrawn from the bio-reactor, and the liquid product is separated from the fermentation broth. The separation can be achieved by any suitable method. In some embodiments, the liquid product is separated by distillation. Optionally, the fermenting mixture can be treated. In some instances, the treatment comprises centrifugation to recover the ionophores. In certain embodiments, the treating comprises solids removal to recover ionophores.

In some embodiments, the method of fermenting comprises a fermentation broth, one or more fermenting species, a gaseous substrate, and one or more ionophores.

In some embodiments, the method of fermenting comprises a fermentation broth, media, one or more fermenting species, a gaseous substrate, one or more ionophores.

In some embodiments, the method of fermenting comprises a fermentation broth, one or more fermenting species, one or more competing species, a gaseous substrate, and one or more ionophores.

In some embodiments, the method of fermenting comprises a fermentation broth, media, one or more fermenting species, one or more competing species, a gaseous substrate, and one or more ionophores.

In some embodiments, the fermentation brother has a pH of about 1 to about 6, about 2 to about 6.5, about 3 to about 5, 5 to about 7, or about 7 to about 9.

In an embodiment, the ionophore targets proton gradients.

In some embodiments, the ionophore targets sodium gradients.

In some embodiments, the ionophore targets potassium gradients.

In some embodiments, the ionophore targets sodium gradients and potassium gradients.

In some embodiments, the ionophore targets $Li^+$ gradients, $Mg^{2+}$ gradients, $Ca^{2+}$ gradients, or $NH_4^+$ gradients.

In some embodiments, the one or more fermenting genus can be *Clostridium*.

In some embodiments, the competing genus can be *Moorella* or *Methanococcus*.

The invention also provides a fermentation system for fermenting a gaseous substrate to form a liquid product, the system comprising: (a) a fermentation vessel; (b) a gaseous substrate supply conduit for introducing the gaseous substrate into the fermentation vessel; (c) an aqueous fermentation broth disposed in the fermentation vessel, the fermentation broth comprising a fermenting species; (d) an ionophore supply conduit in communication with the fermentation vessel for introducing at least one type of ionophore into the vessel, the ionophore selected to minimally inhibit the fermenting species from growing and/or producing the liquid product; and (e) a liquid recovery conduit for collecting the liquid product after the gaseous substrate is allowed to ferment.

In some embodiments, the fermentation system comprises a fermentation vessel. The fermentation vessel can be any suitable fermentation vessel, capable of permitting growth of one or more fermenting species. In certain embodiments, the fermentation vessel is a bio-reactor. The fermentation vessel further comprises an aqueous fermentation broth comprising one or more microorganisms.

In some embodiments, the fermentation system comprises a gaseous substrate supply conduit. Typically, the gaseous substrate supply conduit is used to introduce the gaseous substrate to the fermentation vessel. In some embodiments, the gaseous substrate can be added during any step of the fermentation process. In certain embodiments, the gaseous substrate supply conduit further comprises a valve means in relation to the fermentation vessel. The valve means can be any suitable valve means, capable of regulating the continuous, semi-continuous, or segmented introduction of the gaseous substrate.

In some embodiments, the fermentation system comprises an ionophore supply conduit. The ionophore supply conduit is used to introduce at least one type of ionophore to the fermentation vessel. The ionophore can be added during any step of the fermenting process. In certain embodiments, the introduction of the ionophore can be continuous, segmented, semi-continuous, or combinations thereof. In some embodiments, the ionophore supply conduit further introduces media into the fermentation vessel. In some embodiments, the ionophore supply conduit further comprises a valve means in relation to the fermentation vessel. The valve means can be any suitable valve means, capable of regulating the continuous, semi-continuous, or segmented introduction of the ionophore.

In some embodiments, the fermentation system further comprises a liquid recovery conduit. In certain embodiments, the liquid recover conduit is used for collecting the liquid product from the fermentation vessel. In a preferred embodiment, the liquid product is collected after the gaseous substrate is allowed to ferment.

In some instances, the fermentation system further comprises a media supply conduit. The media supply conduit is used to add media to the fermentation vessel. In some embodiments, the introduction of the media can be continuous, segmented, semi-continuous, or combinations thereof. In some embodiments, the media supply conduit further comprises a valve means in relation to the fermentation vessel. The valve means can be any suitable valve means, capable of regulating the continuous, semi-continuous, or segmented introduction of the ionophore.

In some instances, the fermentation system further comprises a base supply conduit. The base supply conduit is used to add one or more bases to the fermentation vessel. In some embodiments, the introduction of the base can be continuous, segmented, semi-continuous, or combinations thereof. In some embodiments, the base supply conduit further comprises a valve means in relation to the fermentation vessel. The valve means can be any suitable valve means, capable of regulating the continuous, semi-continuous, or segmented introduction of the base.

In some instances, the fermentation system further comprises an anti-foaming agent supply conduit. The anti-foaming agent supply conduit is used to add one or more anti-foaming agents to the fermentation vessel. In some embodiments, the introduction of the anti-foaming agent can be continuous, segmented, semi-continuous, or combinations thereof. In some embodiments, the anti-foaming agent supply conduit further comprises a valve means in relation to the fermentation vessel. The valve means can be any suitable valve means, capable of regulating the continuous, semi-continuous, or segmented introduction of the anti-foaming agent.

In some instances, the fermentation system further comprises a distiller. In certain embodiments, the distiller can be in communication with the fermentation vessel to receive the portion of the fermentation mixture withdrawn from the bioreactor. Generally, the distiller is adapted to separate the liquid product from the fermentation mixture by way of distillation. In preferred embodiments, the distiller removes the liquid product while the fermentation process maintains its continuous method.

In an embodiment, the fermentation system comprises a fermentation vessel, a gaseous substrate supply conduit, and an ionophore supply conduit.

In an embodiment, the fermentation system comprises a fermentation vessel, a gaseous substrate supply conduit, an ionophore supply conduit, and a liquid recovery conduit.

In an embodiment, the fermentation system comprises a fermentation vessel, a gaseous substrate supply conduit, an ionophore supply conduit, a liquid recovery conduit, and a distiller.

In an embodiment, the fermentation system comprises a fermentation vessel, a gaseous substrate supply conduit, an ionophore supply conduit, a liquid recovery conduit, a distiller, and a media supply conduit.

In an embodiment, the fermentation system comprises a fermentation vessel, a gaseous substrate supply conduit, an ionophore supply conduit, a liquid recovery conduit, a distiller, a base supply conduit, an anti-foaming agent supply conduit, and a media supply conduit.

The individual components of the fermentation process, for example, the fermentation broth, media, media components, gaseous substrate, base, ionophore, fermenting species, and competing species, are as defined by the parameters set forth herein.

The quantities of the individual components of the fermentation process, for example, the amount of media components, the amount of gaseous substrate, and the amount of base are as defined by the concentrations set forth herein.

The invention is further illustrated by the following exemplary embodiments. However, the invention is not limited by the following embodiments.

(1) A method of fermenting a gaseous substrate to form a liquid product, the method comprising: (a) introducing the gaseous substrate into a bio-reactor, the bio-reactor comprising a fermentation broth therein, the fermentation broth comprising a fermenting species; (b) introducing at least one type of ionophore into the bio-reactor, the ionophore having selectivity for minimally inhibiting the fermenting species from growing and/or producing the liquid product; and (c) allowing the substrate to ferment to produce the liquid product, wherein the gaseous substrate is the primary carbon source for the fermentation product.

(2) A method of fermenting a gaseous substrate to form a liquid product, the method comprising: (a) introducing the gaseous substrate into a bio-reactor, the gaseous substrate comprising at least one of the following constituents: carbon monoxide, carbon dioxide, and hydrogen, the bio-reactor comprising a fermentation broth comprising a fermenting species; (b) introducing at least one type of ionophore into the bio-reactor, the ionophore having selectivity for minimally inhibiting the fermenting species from growing and/or producing an undesired product; and (c) allowing the gaseous substrate to ferment to produce the liquid product, wherein the gaseous substrate is the primary carbon source for the fermentation product.

(3) A method of anaerobically fermenting a gaseous substrate to form a liquid product, the method comprising: (a) introducing the gaseous substrate into a bio-reactor, the bio-reactor comprising a fermentation broth therein, the fermentation broth containing at least two types of microorganisms, one type comprising at least one fermenting species, and the other type comprising at least one competing species; (b) introducing at least one type of ionophore into the bio-reactor, the ionophore having selectivity for preferentially inhibiting the at least one competing species from growing and/or producing an undesired product; and (c) allowing the substrate to ferment by exposure to the at least one fermenting species, to produce the liquid product, wherein the gaseous substrate is the primary carbon source for the fermentation product.

(4) A method of anaerobically fermenting a gaseous substrate to form a liquid product, the method comprising: (a) introducing the gaseous substrate into a bio-reactor, the gaseous substrate comprising at least one of the following constituents: carbon monoxide, carbon dioxide, and hydrogen, the bio-reactor comprising a fermentation broth therein, the fermentation broth containing at least two types of microorganisms, one type comprising at least one fermenting species, and the other type comprising at least one competing species; (b) introducing at least one type of ionophore into the reactor, the ionophore having selectivity for preferentially inhibiting the at least one competing species from growing and/or producing an undesired product; and (c) allowing the gaseous substrate to ferment by exposure to the at least one fermenting species, to produce the liquid product.

(5) The method of embodiment (4), wherein the competing species is a contaminant and the one fermenting species is a C1 fixing microorganism.

(6) The method of embodiment (4) or (5), further comprising introducing media into the bio-reactor.

(7) The method of embodiment (6), wherein the media comprises one or more of the following constituents: at least one vitamin, at least one mineral, and at least one metal.

(8) The method of embodiment (7), wherein the media comprises at least one type of vitamin.

(9) The method of embodiment (8), wherein the at least one type of vitamin comprises a nutrient selected to enhance growth of the at least one fermenting species.

(10) The method of any one of embodiments (7)-(9), wherein the media comprises at least one metal.

(11) The method of embodiment (10), wherein the metal comprises one or more of the following: lithium, manganese, cobalt, nickel, copper, gallium, arsenic, selenium, aluminum, silicon, phosphorous, molybdenum, zirconium, silver, palladium, zinc, tungsten, and cadmium.

(12) The method of any one of embodiments (7)-(11), wherein the media comprises at least one mineral.

(13) The method of embodiment (12), wherein the mineral comprises one or more of any form of the following: nitrogen, calcium, chloride, iron, iodine, potassium, molybdenum, magnesium, sulfur, phosphorous, and sodium.

(14) The method of any one of embodiments (5)-(13), wherein the liquid product is at least one alcohol, at least one acid, or any combination thereof.

(15) The method of embodiment (14), wherein the liquid product is one or more of ethanol, n-propanol, iso-propanol, n-butanol, iso-butanol, n-pentanol, n-hexanol acetic acid, propanoic acid, butanoic acid, pentatonic acid, and hexanoic acid.

(16) The method of embodiment (15), wherein the liquid product is ethanol.

(17) The method of embodiment (15), wherein the liquid product is butanol.

(18) The method of any one of embodiments (5)-(17), wherein the pH of the fermentation broth is from about 1 to about 9.

(19) The method of embodiment (18), wherein the pH is from about 2 to about 7.

(20) The method of embodiment (18), wherein the pH is from about 3 to about 7.

(21) The method of embodiment (18), wherein the pH is from about 2 to about 6.

(22) The method of any one of embodiments (1)-(21), further comprising introducing a base into the bio-reactor.

(23) The method of embodiment (22), wherein the base comprises hydroxide ions.

(24) The method of embodiment (22), wherein the base comprises one or more of lithium hydroxide, sodium hydroxide, potassium hydroxide, magnesium hydroxide, calcium hydroxide, lithium bicarbonate, sodium bicarbonate, and potassium bicarbonate.

(25) The method of any one of embodiments (1)-(24), wherein the gaseous substrate is syngas.

(26) The method of any one of embodiments (1)-(25), wherein at least a portion of the gaseous substrate is prepared from gasification of solid substrate.

(27) The method of embodiment (26), wherein the gasified solid substrate is one or more of the following: biomass, coal, woodchips, or municipal solids.

(28) The method of any one of embodiments (1)-(27), wherein at least a portion of the gaseous substrate is prepared from reforming a gaseous precursor.

(29) The method of embodiment (28), wherein steam is used in the reforming.

(30) The method of embodiment (28), wherein oxygen is used in the reforming.

(31) The method of embodiment (28), wherein the gaseous precursor is methane.

(32) The method of any one of embodiments (1)-(31), wherein at least a portion of the gaseous substrate is prepared from coal.

(33) The method of any one of embodiments (1)-(32), wherein the gaseous substrate is scrubbed prior to introduction into the bio-reactor.

(34) The method of embodiment (33), wherein the gaseous precursor is scrubbed.

(35) The method of embodiment (1)-(34), wherein the gaseous substrate is partially oxidized.

(36) The method of any one of embodiments (1)-(35), wherein the fermenting species is an acetogen, homoacetogen, or combinations thereof.

(37) The method of embodiment (36), wherein the fermenting species comprises one or more of the following: *Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii, Butyribacterium methylotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum*, and *Treponema primitia*.

(38) The method of any one of embodiments (1)-(37), wherein the competing species comprises one or more of the following: *Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii,*

*Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum,* and *Treponema primitia.*

(390) The method of any of embodiments (1)-(38), wherein the competing species uses sodium gradients for adenosine triphosphate (ATP) production, and wherein the ionophore inhibits the sodium gradients from producing ATP.

(40) The method of any one of embodiments (1)-(39), wherein the fermenting species uses hydrogen gradients for ATP production.

(41) The method of any one of embodiments (1)-(40), wherein the ionophore is an antibiotic.

(42) The method of any one of embodiments (1)-(41), wherein the ionophore can be one or more of the following: 12-crown-4, 15-crown-6, 18-crown-6, dibenzo-18-crown-6, and diaza-18-crown-6, A23187, 4-bromo-A23187, alamethicin, beauvericin, bapta(AM), calcimycin, cezomycin, carbonyl cyanide m-chlorophenyl hydrazone, CA 1001, enniatin, gramicidin A, hellebrin, ionomycin, lasalocid, monesin, nigericin, nonactin, phenamil methanesulfonate, salinomycin, tetonasin, ETH2120, ETH 227, ETH 157, 2,3:11,12-Didecalino-16-crown-5, DD-16-C-5, ETH 4120, Dodecylmethylmalonic acid bis[(12-crown-4)methyl ester], Bis[(12-crown-4)methyl]2,2-didodecylmalonate, 4-tert-Butylcalix[4]arene-tetraacetic acid tetraethyl ester, BME 44, and valinomycin.

(43) The method of any one of embodiments (1)-(42), wherein the ionophore is introduced in a liquid feed.

(44) The method of embodiment (43), wherein the ionophore is present in the liquid feed in a concentration of less than about 100 mM.

(45) The method of any one of embodiments (1)-(44), further comprising introducing anti-foaming agent into the bio-reactor.

(46) The method of any one of embodiments (1)-(45), wherein the fermentation broth further contains water.

(47) The method of any one of embodiments (1)-(46), wherein the ionophore is soluble in the fermentation broth.

(48) The method of any one of embodiments (1)-(46), wherein the ionophore is immobilized and/or insoluble in the fermentation broth.

(49) The method of any one of embodiments (1)-(48), wherein the liquid product is produced by a microorganism within the fermentation broth to form a fermentation mixture.

(50) The method of embodiment (51), wherein a portion of the fermentation mixture is withdrawn from the bioreactor, and the liquid product is separated from the fermentation mixture.

(51) The method of embodiment (50), wherein the separation is by distillation.

(52) The method of embodiment (51), wherein, the fermentation mixture is treated.

(53) The method of embodiment (52), wherein the treating comprises centrifuging to recover the immobilized and/or insoluble ionophores.

(54) The method of embodiment (53), wherein the treating comprises solids removal to recover ionophores.

(55) The method of any one of embodiments (1)-(54), wherein the introduction of the ionophore is continuous.

(56) The method of any one of embodiments (1)-(54), wherein the introduction of the ionophore is segmented.

(57) The method of any one of embodiments (1)-(54), wherein the introduction of the ionophore is semi-continuous.

(58) The method of any one of embodiments (1)-(57), wherein the introduction of the gaseous substrate is continuous.

(59) The method of any one of embodiments (1)-(57), wherein the introduction of the gaseous substrate is segmented.

(60) The method of any one of embodiments (1)-(57), wherein the introduction of the gaseous substrate is semi-continuous.

(61) The method of any one of embodiments (1)-(60), wherein the ionophore is immobilized in a porous particle.

(62) The method of embodiment (1)-(61), wherein the immobilization is by using the electron force between the ionophore and the porous particle.

(63) A fermentation system for fermenting a gaseous substrate to form a liquid product, the system comprising: (a) a fermentation vessel; (b) a gaseous substrate supply conduit for introducing the gaseous substrate into the fermentation vessel; (c) an aqueous fermentation broth disposed in the fermentation vessel, the fermentation broth comprising a fermenting species; (d) an ionophore supply conduit in communication with the fermentation vessel for introducing at least one type of ionophore into the vessel, the ionophore selected to minimally inhibit the fermenting species from growing and/or producing the liquid product; and (e) a liquid recovery conduit for collecting the liquid product after the gaseous substrate is allowed to ferment.

(64) A fermentation system for fermenting a gaseous substrate to form a liquid product, the system comprising: (a) a fermentation vessel; (b) a gas supply conduit for introducing the gaseous substrate into the fermentation vessel, the gaseous substrate comprising at least one of the following constituents: carbon monoxide, carbon dioxide, and hydrogen; (c) an aqueous fermentation broth disposed in the fermentation vessel, the fermentation broth comprising a fermenting species; (d) an ionophore supply conduit in communication with the fermentation vessel for introducing at least one type of ionophore into the vessel, the ionophore selected to minimally inhibit the fermenting species from growing and/or producing the liquid product; and (e) a liquid recovery conduit for collecting the liquid product after the gaseous substrate is allowed to ferment.

(65) A fermentation system for anaerobically fermenting a gaseous substrate to form a liquid product, the system comprising: (a) a fermentation vessel; (b) a gaseous substrate supply conduit for introducing the gaseous substrate into the fermentation vessel; (c) an aqueous fermentation broth disposed in the fermentation vessel, the fermentation broth containing at least two types of microorganisms, one type comprising at least one fermenting species, and the other type comprising at least one competing species; (d) an ionophore supply conduit in communication with the fermentation vessel for introducing at least one type of ionophore into the vessel, the ionophore having selectivity for preferentially inhibiting the at least one competing species from growing and/or producing an undesired product; and (e) a liquid recovery conduit for collecting the liquid product after the gaseous substrate is allowed to ferment by exposure to the at least one fermenting species.

(66) A fermentation system for anaerobically fermenting a gaseous substrate to form a liquid product, the system comprising: (a) a fermentation vessel; (b) a gas supply conduit for introducing the gaseous substrate into the fermentation vessel, the gaseous substrate comprising at least one of the following constituents: carbon monoxide, carbon dioxide, and hydrogen; (c) an aqueous fermentation broth disposed in the fermentation vessel, the fermentation broth containing at least two types of microorganisms, one type comprising at least one fermenting species, and the other type comprising at least one competing species; (d) an ionophore supply conduit in communication with the fermentation vessel for introducing at least one type of ionophore into the vessel, the ionophore having selectivity for preferentially inhibiting the at least one competing species from growing and/or producing an undesired product; and (e) a liquid recovery conduit for collecting the liquid product after the gaseous substrate is allowed to ferment by exposure to the at least one fermenting species.

(67) The system of embodiment (66), wherein the ionophore supply conduit further introduces media into the vessel.

(68) The system of embodiment (67), further comprising a media supply conduit, for introducing media into the vessel.

(69) The system of embodiment (67) or (68), wherein the media comprises one or more of the following constituents: at least one vitamin, at least one mineral, and at least one metal.

(70) The system of embodiment (69), wherein the media comprises at least one type of vitamin.

(71) The system of embodiment (70), wherein the at least one type of vitamin comprises a nutrient selected to enhance growth of the at least one fermenting species.

(72) The system of any one of embodiments (69)-(71), wherein the media comprises at least one metal.

(73) The system of embodiment (72), wherein the metal comprises one or more of the following: lithium, manganese, cobalt, nickel, copper, gallium, arsenic, selenium, aluminum, silicon, phosphorous, molybdenum, zirconium, silver, palladium, zinc, tungsten, and cadmium.

(74) The system of any one of embodiments (69)-(73), wherein the media comprises at least one mineral.

(75) The system of embodiment (74), wherein the mineral comprises one or more of the following: nitrogen, calcium, chloride, iron, iodine, potassium, molybdenum, magnesium, sulfur, phosphorous, and sodium.

(76) The system of any one of embodiments (66)-(75), wherein the liquid product comprises at least one alcohol, acid, or any combination thereof.

(77) The system of embodiment (76), wherein the liquid product is one or more of ethanol, n-propanol, iso-propanol, n-butanol, iso-butanol, n-pentanol, n-hexanol, acetic acid, propanoic acid, butanoic acid, pentatonic acid, and hexanoic acid.

(78) The system of embodiment (77), wherein the liquid product is ethanol.

(79) The system of embodiment (77), wherein the liquid product is butanol.

(80) The system of any one of embodiments (66)-(79), wherein the pH of the fermentation broth is from about 1 to about 9.

(81) The system of embodiment (80), wherein the pH is from about 2 to about 7.

(82) The system of embodiment (80), wherein the pH is from about 3 to about 7.

(83) The system of embodiment (80), wherein the pH is from about 2 to about 6.

(84) The system of any one of embodiments (66)-(83), further comprising a base supply conduit for introducing a base and/or a broth into the vessel.

(85) The system of embodiment (84), wherein the base comprises hydroxide ions.

(86) The system of embodiment (85), wherein the base comprises one or more of lithium hydroxide, sodium hydroxide, potassium hydroxide, magnesium hydroxide, calcium hydroxide, lithium bicarbonate, sodium bicarbonate, and potassium bicarbonate.

(87) The system of any one of embodiments (66)-(86), wherein the gaseous substrate is syngas.

(88) The system of any one of embodiments (66)-(87), wherein at least a portion of the gaseous substrate is prepared from gasification of solid gaseous substrate.

(89) The system of embodiment (88), wherein the solid gaseous substrate is one or more of the following: biomass, coal, woodchips, or municipal solids.

(90) The system of any one of embodiments (66)-(89), wherein at least a portion of the gaseous substrate is prepared from reforming a gaseous precursor.

(91) The system of embodiment (90), wherein steam is used in the reforming.

(92) The system of embodiment (90), wherein oxygen is used in the reforming.

(93) The system of embodiment (90), wherein the gaseous precursor is methane.

(94) The system of any one of embodiments (66)-(93), wherein at least a portion of the gaseous substrate is prepared from coal.

(95) The system of embodiment (66-94), wherein the gaseous substrate is partially oxidized.

(96) The system of any one of embodiments (66)-(95), wherein the gaseous substrate is scrubbed prior to introduction into the bio-reactor.

(97) The system of embodiment (96), wherein the gaseous precursor is scrubbed.

(98) The system of any one embodiments (66)-(97), wherein the fermenting species is an acetogen, homoacetogen, or combinations thereof.

(99) The system of embodiment (98), wherein the fermenting species comprises one or more of the following: *Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii, Butyribacterium methylotrophicum, Caldanaerobacter subterraneous, Caldanaerobacter subterraneous pacificus, Carboxydothermus hydrogenoformans, Clostridium aceticum, Clostridium* acetobutylieum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum, and Treponema primitia.

(100) The system of any one of embodiments (66)-(99), wherein the competing species comprises one or more of the following: Acetitomaculum ruminis, Acetoanaerobium noterae, Acetogenium kivui, Acetoanaerobium noterae, Acetohalobium arabaticum, Acetobacterium woodii, Acetobacterium carbinolicum, Acetobacterium malicum, Acetobacterium wieringae, Acetobacterium psammolithicum, Acetobacterium fimetarium, Acetobacterium paludosum, Acetobacterium tundrae, Acetobacterium bakii, Acetonema longum, Alkalibaculum bacchi, Blautia coccoides, Blautia hydrogenotrophica, Blautia producta, Blautia schenckii, Butyribacterium methylotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum, Clostridium autoethanogenum, Clostridium carboxidivorans, Clostridium coskatii, Clostridium difficile, Clostridium drakei, Clostridium formicaceticum, Clostridium glycolicum, Clostridium ljungdahlii, Clostridium magnum, Clostridium mayombei, Clostridium methoxybenzovorans, Clostridium pasteurianum, Clostridium ragsdalei, Clostridium scatologenes, Clostridium thermoaceticum, Clostridium ultunense, Desulfotomaculum kuznetsovii, Eschericichia coli, Eubacterium aggregans, Eubacterium limosum, Fuchsiella alkaliacetigena, Geobacter sulfurreducens, Holophaga foetida, Methanosarcina acetivorans, Methanosarcina barkeri, Moorella mulderi, Moorella thermoacetica, Moorella thermoautotrophica, Oxobacter pfennigii, Peptostreptococcus productus, Ruminococcus productus, Sporomusa paucivorans, Sporomusa sphaeroides, Sporomusa malonica, Sporomusa termitida, Sporomusa ovata, Sporomusa silvacetica, Sporomusa acidovorans, Sporomusa rhize, Thermoanaerobacter kivui, Thermoacetogenium phaeum, and Treponema primitia.

(101) The system of any of embodiments (66)-(100), wherein the competing species uses sodium gradients for adenosine triphosphate (ATP) production, and wherein the ionophore inhibits the sodium gradients from producing ATP.

(102) The system of any one of embodiments (66)-(101), wherein the fermenting species uses hydrogen gradients for ATP production.

(103) The system of any one of embodiments (66)-(102), wherein the ionophore is an antibiotic.

(104) The system of any one of embodiments (67)-(103), wherein the ionophore can be one or more of the following: 12-crown-4, 15-crown-6, 18-crown-6, dibenzo-18-crown-6, and diaza-18-crown-6, A23187, 4-bromo-A23187, alamethicin, beauvericin, bapta(AM), calcimycin, cezomycin, carbonyl cyanide m-chlorophenyl hydrazone, CA 1001, enniatin, gramicidin A, hellebrin, ionomycin, lasalocid, monesin, nigericin, nonactin, phenamil methanesulfonate, salinomycin, tetonasin, ETH2120, ETH 227, ETH 157, 2,3:11,12-Didecalino-16-crown-5, DD-16-C-5, ETH 4120, Dodecylmethylmalonic acid bis[(12-crown-4)methyl ester], Bis[(12-crown-4)methyl]2,2-didodecylmalonate, 4-tert-Butylcalix[4]arene-tetraacetic acid tetraethyl ester, BME 44 and valinomycin.

(105) The system of any one of embodiments (66)-(104), wherein the ionophore is introduced in a liquid feed.

(106) The system of embodiment (105), wherein the ionophore is present in the liquid feed in a concentration of less than about 100 mM.

(107) The system of any one of embodiments (66)-(106), further comprising an anti-foaming agent supply conduit for introducing anti-foaming agent into the vessel.

(108) The system of any one of embodiments (66)-(107), wherein the ionophore is soluble in the fermentation broth.

(109) The system of any one of embodiments (66)-(107), wherein the ionophore is immobilized and/or insoluble in the fermentation broth.

(110) The system of any one of embodiments (66)-(109), wherein the liquid product is produced by a microorganism within the fermentation broth to form a fermentation mixture.

(111) The system of embodiment (110), wherein a portion of the fermentation mixture is withdrawn from the bioreactor.

(112) The system of embodiment (110), further comprising a distiller, the distiller in communication with the vessel to receive the portion of the fermentation mixture withdrawn from the bioreactor, wherein the distiller is adapted to separate the liquid product from the fermentation mixture.

(113) The system of embodiment (112), further comprising treatment means for treating the fermentation mixture.

(114) The system of embodiment (113), wherein the treatment means comprises a centrifuge for recovering the immobilized and/or insoluble ionophores.

(115) The system of any one of embodiments (66)-(114), further comprising valve means in relation to the ionophore supply conduit, the valve means for regulating the continuous, semi-continuous, or staggered introduction of the ionophore.

(116) The system of any one of embodiments (66)-(115), further comprising valve means in relation to the gas supply conduit for regulating the continuous, semi-continuous, or staggered introduction of the gaseous substrate.

(117) The system of any one of embodiments (66)-(116), wherein the ionophore is immobilized in or on a porous particle.

(118) The system of any one of embodiments (66)-(117), wherein the immobilization is by using the electron force between the ionophore and the porous particle.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

EXAMPLES

The following examples are illustrative of specific embodiments of the invention, and various uses thereof.

They are set forth for explanatory purposes only, but, of course, should not be construed as in any way limiting its scope.

Example 1

Contamination Control Using a 20 µM Slug Dose at Steady State Operation

An ionophore, such as a sodium specific ionophore (e.g., monensin), is added to a 2 liter bio-reactor which contains a homoacetogen, such as *Clostridium autoethanogenum*. Experiment A is the control. A competing species of an acetate only producer, such as *Acetobacterium woodii*, is added to a bio-reactor in Experiment B. Experiment B demonstrates that ionophores can be used to inhibit targeted populations of microorganisms in a bio-reactor. Experiment C utilizes a contaminated homoacetogen reactor with the competing species being supplied via an unknown environmental sample. Experiment C demonstrates that the ionophore has a selection for the process homoacetogen over numerous contaminants.

Experiment A

Once reaching a steady state operation of the bio-reactor, the ionophore is added as a slug dose (20 µM total). The bio-reactor contains a fermenting species, such as *Clostridium autoethanogenum*. The results demonstrate that the homoacetogen is not inhibited by the addition of the ionophore.

Experiment B

Two bio-reactors are used. The medium is supplemented with 0.25% yeast extract. A Competing species, such as an *Acetobacterium woodii* type homoacetogen, is inoculated on top of the fermenting species (e.g., a *Clostridium* strain) for both reactors. Once steady state operation is reached, the ionophore is supplemented to one of the tanks as a slug dose (20 µM total). Genetic sequencing and evaluation of the product composition (selection for alcohols) is used to determine the efficacy of the dose. The results demonstrate that the ionophore inhibits the competing species (e.g., *Acetobacterium* strain) and does not inhibit the fermenting species (e.g., *Clostridium* strain). The bio-reactor with the ionophore makes at least 10% more ethanol than the ionophore-free bio-reactor over the time of contamination. Genetic sequencing shows that the competing species is present in the ionophore-free bio-reactor but is washed-out from the ionophore supplemented bio-reactor.

Experiment C

Two bio-reactors are used. The medium is supplemented with 0.25% yeast extract and an environmental sample is inoculated on top of the production strain for both bio-reactors. Once reaching a steady rate operation, a selection of ionophores is supplemented to one of the bio-reactors as a slug dose (20 µM total). Evaluation of product composition (selection for alcohols) is used to determine the efficacy of the dose. The results demonstrate that the ionophore receiving bio-reactor produces 10% more ethanol and loses no electrons to unintended products.

Example 2

Contamination Control Using a Continuous Dose at Steady State Operation

An ionophore, such as a sodium specific ionophore (e.g., monensin), is added to a 2 liter bio-reactor which contains a homoacetogen, such as *Clostridium autoethanogenum*. Experiment D is the control. A competing species of an acetate only producer, such as *Acetobacterium woodii*, is added to a bio-reactor in Experiment E. Experiment E demonstrates that ionophores can be used to inhibit targeted populations of microorganisms in a bio-reactor. Experiment F utilizes a contaminated homoacetogen reactor with the competing species being supplied via an unknown environmental sample. Experiment F demonstrates that the ionophore has a selection for the process homoacetogen over numerous contaminants.

Experiment D

Once reaching a steady state operation of the bio-reactor, the ionophore is added as a continuous dose with a final concentration in the bio-reactor of 20 µM. The bio-reactor contains a fermenting species, such as *Clostridium autoethanogenum*. The results demonstrate that the homoacetogen is not inhibited by the addition of the ionophore.

Experiment E

Two bio-reactors are used. The medium is supplemented with 0.25% yeast extract. A Competing species, such as an *Acetobacterium woodii* type homoacetogen, is inoculated on top of the fermenting species (e.g., a *Clostridium* strain) for both reactors. Once steady state operation is reached, the ionophore is added as a continuous dose with a final concentration in the bio-reactor of 20 µM. Genetic sequencing and evaluation of the product composition (selection for alcohols) is used to determine the efficacy of the dose. The results demonstrate that the ionophore inhibits the competing species (e.g., *Acetobacterium* strain) and does not inhibit the fermenting species (e.g., *Clostridium* strain). The bio-reactor with the ionophore makes at least 10% more ethanol than the ionophore-free bio-reactor over the time of contamination. Genetic sequencing shows that the competing species is present in the ionophore-free bio-reactor but is washed-out from the ionophore supplemented bio-reactor.

Experiment F

Two bio-reactors are used. The medium is supplemented with 0.25% yeast extract and an environmental sample is inoculated on top of the production strain for both bio-reactors. Once reaching a steady rate operation, a selection of ionophores is added as a continuous dose with a final concentration in the bio-reactor of 20 µM. Evaluation of product composition (selection for alcohols) is used to determine the efficacy of the dose. The results demonstrate that the ionophore receiving bio-reactor produces 10% more ethanol and loses no electrons to unintended products.

Example 3

Contamination Control Using a Slug Dose at Start-Up of a Bio-Reactor

An ionophore, such as a sodium specific ionophore (e.g., monensin), is added to a 2 liter bio-reactor which contains a homoacetogen, such as *Clostridium autoethanogenum*. Experiment G is the control. A competing species of an acetate only producer, such as *Acetobacterium woodii*, is added to a bio-reactor in Experiment H. Experiment H demonstrates that ionophores can be used to inhibit targeted populations of microorganisms in a bio-reactor. Experiment I utilizes a contaminated homoacetogen reactor with the competing species being supplied via an unknown environmental sample. Experiment I demonstrates that the ionophore has a selection for the process homoacetogen over numerous contaminants.

Experiment G

The ionophore is added to one of the tanks at the start-up of the bio-reactor as slug dose of 5 µM. The bio-reactor contains a fermenting species, such as *Clostridium autoethanogenum*. The results demonstrate that the homoacetogen is not inhibited by the addition of the ionophore.

Experiment H

Two bio-reactors are used. The medium is supplemented with 0.25% yeast extract. A Competing species, such as an *Acetobacterium woodii* type homoacetogen, is inoculated on top of the fermenting species (e.g., a *Clostridium* strain) for both reactors. The ionophore is added to one of the tanks at the start-up of the bio-reactor as slug dose of 5 µM. Genetic sequencing and evaluation of the product composition (selection for alcohols) is used to determine the efficacy of the dose. The results demonstrate that the ionophore inhibits the competing species (e.g., *Acetobacterium* strain) and does not inhibit the fermenting species (e.g., *Clostridium* strain). The bio-reactor with the ionophore makes at least 10% more ethanol than the ionophore-free bio-reactor over the time of contamination. Genetic sequencing shows that the competing species is present in the ionophore-free bio-reactor but is washed-out from the ionophore supplemented bio-reactor.

Experiment I

Two bio-reactors are used. The medium is supplemented with 0.25% yeast extract. A competing species, such as an *Acetobacterium woodii* type homoacetogen, is inoculated on top of the production strain for both reactors. The ionophore is added to one of the tanks at the start-up of the bio-reactor as slug dose of 5 µM. Evaluation of product composition (selection for alcohols) is used to determine the efficacy of this dose. The results demonstrate that the control bio-reactor receiving no ionophore produces approximately 5% more acetic acid as it was entering steady state operation.

Example 4

Contamination Control Using a Continuous Dose at Start-Up of a Bio-Reactor

Two bio-reactors are used. The medium is supplemented with 0.25% yeast extract. A competing species, such as an *Acetobacterium woodii* type homoacetogen, is inoculated on top of the production strain for both reactors. An ionophore, such as a sodium specific ionophore (e.g., monensin), is added to one of the tanks at the start-up of the bio-reactor as a continuous dose that is adjusted based on the evaluation of product composition (selection for alcohols). The dosing guidelines can be a relationship to OD, with the flow rate of the 20 mM ionophore solution varying to keep the concentration in the bio-reactor at 6 µM/OD. The results demonstrate that the ionophore supplemented reactor does not allow for the undesired competing species (e.g., *Acetobacterium* microorganism) to grow. The control bio-reactor receiving no ionophore produced approximately 10% more acetic acid, presumably due to the competing species (i.e., *Acetobacterium*) contamination.

Example 5

Figure 1:
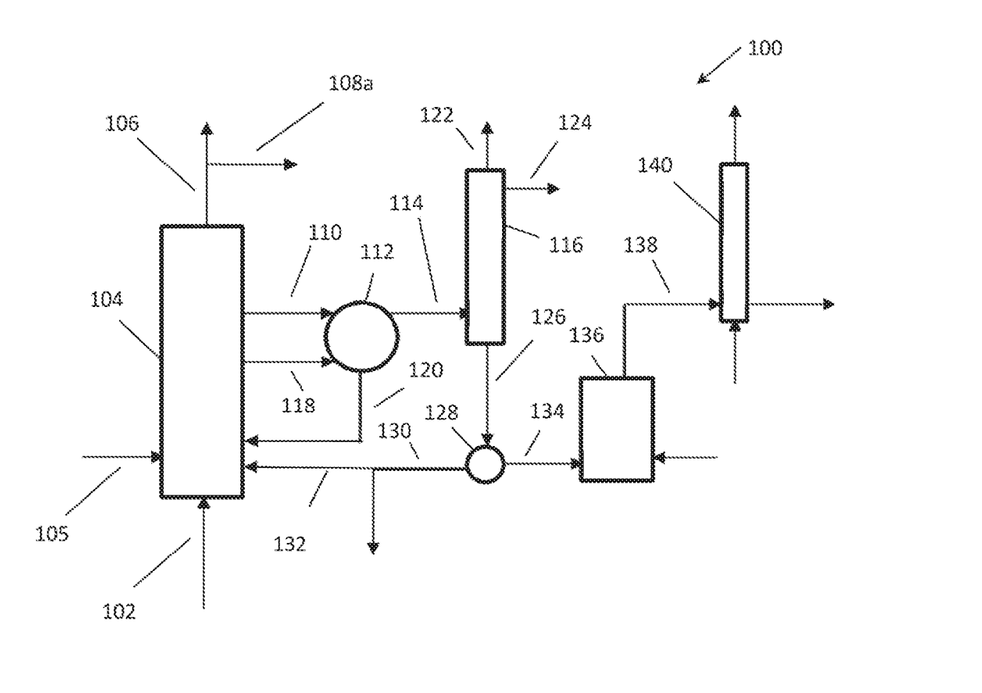
FIG. 1 is a schematic depiction of an apparatus for supplying an ionophore during bioconversion of a gaseous substrate to form a liquid product.

An illustrative embodiment of the system and its application may be facilitated by reference to FIG. 1. FIG. 1 is a schematic depiction of an apparatus generally designated as 100 suitable for practicing processes in accordance with this invention for the production and recovery of at least one liquid product from anaerobic bioconversion of syngas. The invention can be operated in either continuous or batch mode. FIG. 1 omits minor equipment such as pumps, compressors, valves, instruments, the exchangers and other devices the placement of which and the operation thereof are well known to those practiced in chemical engineering. FIG. 1 also omits ancillary unit operations.

Syngas is provided to fermentation reactor 104 via line 102. Fermentation reactor 104 is adapted to hold an aqueous fermentation broth and microorganisms for fermenting a gaseous substrate to at least one liquid product. An off gas, which generally comprises nitrogen, methane, and unreacted hydrogen, carbon dioxide and carbon monoxide, is withdrawn from fermentation reactor 104 via line 106. All, or a portion of the off-gas in line 106 is directed via line 108 for further processing. At least one ionophore is added to fermenter 104 via line 105 as required.

A portion of the aqueous fermentation broth in fermentation reactor 104 is withdrawn via line 110, heated in heat pump assembly 112, and then passed via line 114 to distillation assembly 116. Heat pump assembly comprises indirect heat exchangers from which a heat pump removes heat or into which the heat pump introduces heat. Fermentation broth is withdrawn from fermentation reactor 104 via line 118 and cooled in heat pump assembly 112 and returned via line 120 to fermentation reactor 104. Thus heat from the exothermic fermentation is removed and is used to increase the temperature of the aqueous fermentation broth passing to distillation assembly 116 which in turn reduces the heat required to be supplied by other unit operations (not shown) in the distillation assembly for the distillation assembly while concurrently decreasing external cooling requirements of the broth in fermenter 104.

Distillation assembly 116 separates the product from the aqueous phase and provides is withdrawn via line 124. Non-condensables exit distillation assembly 116 via line 122. The heat in the distillation assembly 116 kills the microorganisms used for the fermentation of the gaseous substrate. A bottoms stream (aqueous distillation fraction) containing solids from the microorganisms, the at least one immobilized and/or insoluble ionophore, and proteins precipitated from solution in an aqueous phase is passed via line 126 to a solids separation unit operation 128, which for purposes of discussion is a centrifuge. The solids depleted fraction containing the ionophore is withdrawn from the centrifuge is via line 130 and can be returned to fermentation reactor 104 via line 132. The solids fraction from solids separation unit operation 128 is transported via line 134 to anaerobic digester 136.

Anaerobic digester 136 generates a biogas comprising methane and reduces the solids generated by the fermentation. Biogas generated in anaerobic digester 136 is passed via line 138 to biogas scrubber 140 to remove hydrogen sulfide.

It will be understood that this example merely illustrates an embodiment of the system and its applications. Other variations and modifications of the system and its applications will be readily apparent to one of ordinary skill in the art from the full description herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The organizational formatting characters used herein (for example, a., b., c., (a), (b), (c), 1, 2, and 3) do not imply sequential steps unless already explicitly stated.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of anaerobically fermenting a syngas to form a liquid product comprising an alcohol or acid, the method comprising:
   a. introducing the syngas into a bio-reactor, wherein the syngas comprises carbon monoxide, carbon dioxide, and hydrogen,
   i. the bio-reactor comprising a fermentation broth therein, the fermentation broth containing at least two types of microorganisms, one type comprising at least one fermenting microorganism species, and the other type comprising at least one competing microorganism species;
   b. introducing at least one type of ionophore into the bio-reactor, the ionophore having selectivity for preferentially inhibiting the at least one competing microorganism species from growing and/or producing an undesired product; and
   c. allowing the syngas to ferment by exposure to the at least one fermenting microorganism species, to produce the liquid product; wherein:
   the fermenting species is *Clostridium autoethanogenum*; and
   the competing species is *Acetobacterium woodii*.

2. The method of claim 1, wherein the competing species is a contaminant and the one fermenting species is a C1 fixing microorganism.

3. The method of claim 2, further comprising introducing media into the bio-reactor.

4. The method of claim 1, wherein the liquid product is one or more of ethanol, n-propanol, iso-propanol, n-butanol, iso-butanol, n-pentanol, n-hexanol, acetic acid, propanoic acid, butanoic acid, pentatonic acid, and hexanoic acid.

5. The method of claim 1, wherein the competing species uses sodium gradients for adenosine triphosphate (ATP) production, and wherein the ionophore inhibits the sodium gradients from producing ATP.

6. The method of claim 1, wherein the fermenting species uses hydrogen gradients for ATP production.

7. The method of claim 1, wherein the ionophore is one or more of the following: 12-crown-4, 15-crown-6, 18-crown-6, dibenzo-18-crown-6, and diaza-18-crown-6, A23187, 4-bromo-A23187, alamethicin, beauvericin, bapta (AM), calcimycin, cezomycin, carbonyl cyanide m-chlorophenyl hydrazone, CA 1001, enniatin, gramicidin A, hellebrin, ionomycin, lasalocid, monensin, nigericin, nonactin, phenamil methanesulfonate, salinomycin, tetonasin, ETH2120, ETH 227, ETH 157, 2,3:11,12-Didecalino-16-crown-5, DD-16-C-5, ETH 4120, Dodecylmethylmalonic acid bis[(12-crown-4)methyl ester], Bis[(12-crown-4) methyl] 2,2-didodecylmalonate, 4-tert-Butylcalix[4]arene-tetraacetic acid tetraethyl ester, BME 44 and valinomycin.

8. A fermentation system for anaerobically fermenting a syngas to form a liquid product, the system comprising:
   a. a fermentation vessel;
   b. a syngas supply conduit for introducing the syngas into the fermentation vessel;
   c. an aqueous fermentation broth disposed in the fermentation vessel, the fermentation broth containing at least two types of microorganisms, one type comprising at least one fermenting species, and the other type comprising at least one competing species;
   d. an ionophore supply conduit in communication with the fermentation vessel for introducing at least one type of ionophore into the vessel, the ionophore having selectivity for preferentially inhibiting the at least one competing species from growing and/or producing an undesired product; and
   e. a liquid recovery conduit for collecting the liquid product after the syngas is allowed to ferment by exposure to the at least one fermenting species;
   the fermenting species is *Clostridium autoethanogenum*; and
   the competing species is *Acetobacterium woodii*.

9. The system of claim 8, wherein the liquid product is at least one alcohol, at least one acid, or any combination thereof.

10. The system of claim 8, wherein the liquid product is one or more of ethanol, n-propanol, iso-propanol, n-butanol, iso-butanol, n-pentanol, n-hexanol, acetic acid, propanoic acid, butanoic acid, pentatonic acid, and hexanoic acid.

11. The system of claim 8, wherein the pH is from about 3 to about 7.

12. The system of claim 8, wherein the fermenting species uses hydrogen gradients for ATP production.

13. The system of claim 8, wherein the ionophore is one or more of the following: 12-crown-4, 15-crown-6, 18-crown-6, dibenzo-18-crown-6, and diaza-18-crown-6, A23187, 4-bromo-A23187, alamethicin, beauvericin, bapta (AM), calcimycin, cezomycin, carbonyl cyanide m-chlorophenyl hydrazone, CA 1001, enniatin, gramicidin A, hellebrin, ionomycin, lasalocid, monensin, nigericin, nonactin, phenamil methanesulfonate, salinomycin, tetonasin, ETH2120, ETH 227, ETH 157, 2,3:11, 12-Didecalino-16-crown-5, DD-16-C-5, ETH 4120, Dodecylmethylmalonic acid bis[(12-crown-4)methyl ester], Bis[(12-crown-4)methyl] 2,2-didodecylmalonate, 4-tert-Butylcalix[4]arene-tetraacetic acid tetraethyl ester, BME 44 and valinomycin.

14. The system of claim 8, wherein at least a portion of the syngas is prepared from coal.

15. The system of claim 8, wherein the syngas contains at least one of the following: water vapor, nitrogen, methane, ammonia, and hydrogen sulfide.

16. The method of claim 1, wherein at least a portion of the syngas is prepared from coal.

17. The method of claim 1, wherein the syngas contains at least one of the following: water vapor, nitrogen, methane, ammonia, and hydrogen sulfide.

18. The method of claim 7, wherein the ionophore is monensin.

19. The system of claim 13, wherein the ionophore is monensin.

* * * * *